United States Patent
van Baalen et al.

(10) Patent No.: US 9,320,294 B2
(45) Date of Patent: Apr. 26, 2016

(54) NUTRITIONAL COMPOSITIONS WITH LIPID GLOBULES WITH A CORE COMPRISING VEGETABLE LIPIDS AND A COATING COMPRISING PHOSPHOLIPIDS OR POLAR LIPIDS

(75) Inventors: Antonie van Baalen, Arnhem (NL); Eline Marleen van der Beek, Wageningen (NL); Christopher Beermann, Petersberg (DE); Günther Boehm, Echzell (DE)

(73) Assignee: N.V. Nutricia, Zoetermeer (NL)

( * ) Notice: Subject to any disclaimer, the term of this patent is extended or adjusted under 35 U.S.C. 154(b) by 42 days.

(21) Appl. No.: 13/061,643

(22) PCT Filed: Sep. 2, 2009

(86) PCT No.: PCT/NL2009/050525
§ 371 (c)(1),
(2), (4) Date: May 16, 2011

(87) PCT Pub. No.: WO2010/027258
PCT Pub. Date: Mar. 11, 2010

(65) Prior Publication Data
US 2011/0206743 A1    Aug. 25, 2011

Related U.S. Application Data

(60) Provisional application No. 61/093,548, filed on Sep. 2, 2008.

(30) Foreign Application Priority Data

Sep. 2, 2008 (EP) .................... 08163478

(51) Int. Cl.
| A23L 1/30 | (2006.01) |
| A23L 1/29 | (2006.01) |
| A61K 31/201 | (2006.01) |
| A61K 35/60 | (2006.01) |
| A61K 36/02 | (2006.01) |

(52) U.S. Cl.
CPC ............... *A23L 1/3006* (2013.01); *A23L 1/293* (2013.01); *A23L 1/296* (2013.01); *A61K 31/201* (2013.01); *A61K 35/60* (2013.01); *A61K 36/02* (2013.01)

(58) Field of Classification Search
CPC ....... A23L 1/3006; A23L 1/293; A23L 1/296; A61K 31/201; A61K 35/60; A61K 36/02; A61K 2300/00
See application file for complete search history.

(56) References Cited

U.S. PATENT DOCUMENTS

| 5,709,888 | A | 1/1998 | Gil et al. |
| 2002/0004527 | A1 | 1/2002 | Auestad et al. |
| 2003/0104078 | A1 | 6/2003 | Barrett-Reis et al. |
| 2004/0062820 | A1 | 4/2004 | Lasekan et al. |
| 2005/0037089 | A1 | 2/2005 | Jobbins |
| 2005/0214392 | A1 | 9/2005 | McPeak et al. |
| 2006/0188614 | A1 | 8/2006 | Shapira |
| 2006/0210697 | A1 | 9/2006 | Mower |
| 2007/0073193 | A1 | 3/2007 | Park |
| 2007/0073194 | A1 | 3/2007 | Chen et al. |
| 2008/0064656 | A1 | 3/2008 | Van Tol |
| 2008/0292724 | A1 | 11/2008 | Hageman |
| 2009/0011075 | A1 | 1/2009 | Shulman et al. |
| 2011/0300204 | A1 | 12/2011 | Van Der Beek et al. |

FOREIGN PATENT DOCUMENTS

| EP | 0 333 288 A1 | 9/1989 | |
| EP | 1 252 824 A2 | 10/2002 | |
| EP | WO 2006/094995 | * 9/2006 | ............ A23D 11/06 |
| EP | 1 800 675 A1 | 6/2007 | |
| EP | 1 800 675 A1 | 6/2007 | |
| EP | 2 305 049 | 4/2011 | |
| JP | 2001-158736 | 6/2001 | |
| NL | WO2007073193 | * 6/2007 | ................ A23L 1/29 |
| SU | 1084006 A | 4/1984 | |
| WO | WO 2003/005836 | * 1/2003 | |
| WO | WO-2005/007373 A1 | 1/2005 | |
| WO | WO-2005/051091 A1 | 6/2005 | |
| WO | WO 2005/051091 A1 | 6/2005 | |
| WO | WO-2005/051092 A2 | 6/2005 | |
| WO | WO-2006/052134 A2 | 5/2006 | |
| WO | WO 2006/094995 A1 | 9/2006 | |
| WO | WO-2006/114790 A2 | 11/2006 | |
| WO | WO-2007/073192 A2 | 6/2007 | |
| WO | WO 2007/073193 A2 | 6/2007 | |

(Continued)

OTHER PUBLICATIONS

Simon Joscelyne & Gun Tragardh, Food Emulsions Using Membrane Emulsification: Conditions for Producing Small Droplets, 39 J Food Eng. 59 (1999).*
James Hamilton, Interactions of Triglycerides with Phospholipids: Incorporation into the Bilayer Structure and Formation of Emulsions, 28 Biochem. 2514 (1989).*
Osteoporosis, PubMed Health, available at http;www.ncbi.nlm.nih.gov-pubmedhealth-PMH0001400, 2011.
Database WPI Week 200937, Thomoson Scientific, London, GB, AN 2009-J69887, XP002578379.
Database WPI Week 198447, Thomson Scientific, London, GB; AN 1984-293720 XP002505629 & SU 1 084 006 A (A Med Nutrition Ins) Apr. 7, 1984.
International Search Report mailed Dec. 1, 2009 in corresponding PCT/NL2009/050525.

(Continued)

*Primary Examiner* — Sean Basquill
(74) *Attorney, Agent, or Firm* — Foley & Lardner LLP; Sunit Talapatra

(57) ABSTRACT

The present invention relates to a nutritional composition for infants and/or toddlers comprising a lipid component which has a large lipid globule size. The composition can be used to prevent obesity and/or improve body composition later in life. Said lipid component comprises 10-50 wt % vegetable lipids, and the lipid globules have a volume-weighted diameter above 1.0 m and/or a diameter of 2-12 m in an amount of at least 45 vol %.

15 Claims, No Drawings

(56) References Cited

FOREIGN PATENT DOCUMENTS

| WO | WO-2007/073194 A2 | 6/2007 |
|---|---|---|
| WO | WO-2007/097523 A2 | 8/2007 |
| WO | WO-2008/005033 A1 | 1/2008 |
| WO | WO-2008/054192 A1 | 5/2008 |
| WO | WO-2008/081934 A1 | 7/2008 |
| WO | WO-2009/051502 A1 | 4/2009 |
| WO | WO-2009/057121 A1 | 5/2009 |
| WO | WO-2009/066685 A1 | 5/2009 |
| WO | WO-2009/138680 A2 | 11/2009 |
| WO | WO-2009/015448 A1 | 12/2009 |
| WO | WO-2009/154448 A1 | 12/2009 |
| WO | WO-2010/027258 A1 | 3/2010 |
| WO | WO-2010/027259 A1 | 3/2010 |
| WO | WO-2010/068086 A1 | 6/2010 |
| WO | WO-2010/068103 A1 | 6/2010 |
| WO | WO-2010/068105 A1 | 6/2010 |
| WO | WO 2011/108934 A1 | 9/2011 |

OTHER PUBLICATIONS

Durand, A. et al. "Particle sizes and stability of UHT bovine, cereal and grain milks", Food Hydrocolloids, 2003, vol. 17, pp. 671-678.
Fave, G. et al. "Physicochemical properties of lipids; New strategies to manage fatty acid bioavailability", Cellular and Molecular Biology, 2004, vol. 50, No. 7, pp. 815-831.
McClements, D. "Food Emulsions—Principles, Practices, and Techniques", CRC Press, Second Edition, 2005, Section 7.3.
Michalski, M. et al. "Size Distribution of Fat Globules in Human Colostrum, Breast Milk, and Infant Formula", J. Dairy Sci., 2005, vol. 88, pp. 1927-1940.
Petrowski, G. "Emulson stability and its relation to foods", Emulsion Stability, 1976, pp. 309-359.
Ruegg, et al. "The Fat globule size distribution in human milk", Biochimica et Biophysica Acta, 1981, vol. 666., pp. 7-14.
Schultz, S. et al. "High-Pressure homogenization as a process for emulsion formation", Chem. Eng. Technol., 2004, vol. 27, No. 4, pp. 361-368.
Simonin, C. et al. "Comparison of the fat content and fat globule size distribution of breast milk from mothers delivering term and preterm", The American Journal of Clinical Nutrition, Oct. 1984, vol. 40, pp. 820-826.
Whittlestone, W. et al. "Variations in the Fat Content of Human Milk During Suckling", Ruakura Animal Research Station, Department of Agriculture, pp. 204-206.
Osteoporosis, PubMed Health, available at http;www.ncbi.nlm.nih.gov-pubmedhealth-PMH0001400.
Agostoni et al: "Polyunsaturated Fatty Acids in Human Milk and Neurological Development", Current Pediatric Reviews, vol. 1, 2005, pp. 25-30, XP002643794.
Database WPI Week 200937, Thomoson Scientific, London, GB, AN 2009-J69887, XP002578379, 2010.
Holman et al: "Deficiency of essential fatty acids and membrane fluidity during pregnancy and lactation", Proceedings of the National Acacemy of Sciences of the United States of America, vol. 88, No. 11, Jun. 1, 1991, pp. 4835-4839, XP002620898.
Hur et al.: "Influence of initial emulsifier type on microstructural changes occurring in emulsified lipids during in vitro digestion", Food Chemistry, vol. 114, 2009, pp. 253-262, XP002607759.
Jensen et al: "Specialty Lipids for Infant Nutrition. I. Milks and Formulas", Journal of Pediatric Gastroenterlogy and Nutrition, vol. 15, No. 3, 1992, pp. 232-245, XP002620897.
Makrides et al: "Fatty acid composition of brain, retina, and erythrocytes in breast- and formula-fed infants", American Journal of Clinical Nutrition, US, vol. 60, No. 2, 1994, pp. 189-194, XP002620896.
Mun et al: "Influence of interfacial composition on in vitro digestibility of emulsified lipids: potential mechanism for chitosan's ability to inhibit fat digestion.", Food Biophysics, vol. 1, 2006, pp. 21-29, XP002607758.
Park et al.: "Influence of encapsulation of emulsified lipids with chitosan on their in vivo digestibility.", Food Chemistry, vol. 104, 2007, pp. 761-767, XP002607757.
International Preliminary Report on Patentability for PCT/NL2011/050156—mailed Aug. 24, 2012.
International Preliminary Report on Patentability for PCT/NL2011/050187—mailed Jun. 13, 2012.
International Preliminary Report on Patentability for PCT/NL2011/050188—mailed Jun. 15, 2012.
International Search Report for PCT/NL2011/050156—mailed Jun. 1, 2011.
International Search Report for PCT/NL2011/050187—mailed Jul. 5, 2011.
International Search Report for PCT/NL2011/050188—mailed Jul. 5, 2011.
International Search Report for PCT/NL2009/050756—mailed May 11, 2010.
International Search Report for PCT/NL2009/050754—mailed May 7, 2010.
Benoit, B., et al., "Phospholipid Species and Minor Sterols in French Human Milks," Food Chemistry, 120:684-691 (2010).
Michalski et al., "The Dispersion State of Milk Fat Influences Triglyceride Metabolism in the Rat," European Journal of Nutrition, 44:436-444 (2005).
Michalski et al, "The Supramolecular Structure of Milk Fat Influences Plasma Triacylglycerols and Fatty Acid Profile in the Rat," European Journal of Nutrition, 45:215-224 (2006).
Vickers, M.H. et al., "Supplementation with a Mixture of Complex Lipids Derived from Milk to Growing Rats Results in Improvements in Parameters Related to Growth and Cognition," Nutrition Research, 29:426-432 (2009).
InFat—The premium choice for infant formula—closer to mother's milk, Nov. 2009, AAK Magazine.
International Preliminary Report on Patentability mailed Sep. 17, 2013 in International Application No. PCT/NL2012/050623.
International Search Report mailed Oct. 30, 2012 in International Application No. PCT/NL2012/050623.
Lucas Alan, "Long-Term Programming Effects of Early Nutrition—Implications for the Preterm Infant", Journal of Perinatology (2005) 25, S2-S6.
Marmot, et al. "Effect of breast-feeding on plasma cholesterol and weight in young adults", Journal of Epidemiology and Community Health (1980), vol. 34, pp. 164-167.
Owen, et al. "Infant Feeding and Blood Cholesterol: A Study in Adolescents and a Systematic Review", Pediatrics (2006) vol. 110, pp. 597-608.
International Preliminary Report on Patentability for PCT/NL2009/050343, mailed Jul. 19, 2010 (9 pages).
International Search Report for PCT/NL2009/050343, mailed Jul. 15, 2009 (3 pages).
International Search Report for PCT/NL2009/050526, mailed Dec. 14, 2009 (3 pages).
Michalski et al., "Optical parameters of milk fat globules for laser light scattering measurements," Lait, 2001, 81(6):787-796.
Michalski et al., "Size Distribution of Fat Globules in Human Colostrum, Breast Milk, and Infant Formula," J Dairy Sci, 2005, 88(6):1927-1940.

* cited by examiner

NUTRITIONAL COMPOSITIONS WITH LIPID GLOBULES WITH A CORE COMPRISING VEGETABLE LIPIDS AND A COATING COMPRISING PHOSPHOLIPIDS OR POLAR LIPIDS

FIELD OF THE INVENTION

The invention relates to the field of infant milk formula and growing up milks for preventing obesity later in life.

BACKGROUND

Breast-feeding is the preferred method of feeding infants. However, there are circumstances that make breast-feeding impossible or less desirable. In those cases infant formulae are a good alternative. The composition of modern infant formulae is adapted in such a way that it meets many of the special nutritional requirements of the fast growing and developing infant.

Still it seems that improvements can be made towards the constitution of infant milk formulae. Breast fed infants have a decreased chance of becoming obese later in life, compared to formula fed infants, but little is known about the effects of ingredients in the infant formulae on obesity later in life. So far, most research is dedicated to the role of protein concentration or of the fatty acid composition. Obesity is a major health problem in the Western world. It is a medical condition in which excess has accumulated to the extent that it may have an adverse effect on health, leading to reduced life expectancy and it is associated with many diseases, particularly heart disease and type 2 diabetes. Obesity is a leading preventable cause of death worldwide, with increasing prevalence in adults and children, and authorities view it as one of the most serious public health problems of the 21st century.

The present invention relates to such future healthy body composition.

WO 2007/073194 relates to infant formulae comprising phospholipids, sphingolipids, and cholesterols for the prevention of obesity. WO 2007/073193 relates to infant formulae with specific linoleic acid to alpha-linolenic acid ratio's, low linoleic acid content and comprising phospholipids, sphingolipids, cholesterol and/or choline plus uridine for the prevention of obesity later in life. EP1800675 relates to a composition with polyunsaturated fatty acids, proteins and manganese and/or molybdene for improving membrane composition for the treatment of a wide variety of disorders.

Michalski et al, 2005, J Dairy Sci 88:1927-1940 discloses the size distribution of lipid globules in human milk and infant formula. WO 2005/051091 relates to a lipid combination which upon dispersion or emulsification in an essentially aqueous medium with other ingredients of infant formula forms a substantially homogenous dispersion or emulsion having a lipid globule-containing microstructure which is essentially mimetic of the corresponding globular microstructure of naturally occurring HMF. SU 1084006 discloses food for children and invalid people with a lipid globule size of 4 μM diameter, similar to human milk.

SUMMARY OF THE INVENTION

The inventors surprisingly found that the lipid globule size in infant formulae affects the body composition later in life. Specific selection of the lipid globule size in infant formulae results in a decreased fat mass and/or decreased obesity later in life. Specific selection of the lipid globule size in infant formulae also resulted in an increased lean body mass later in life. When early in life an infant formula of the present invention that comprised lipids with a larger lipid globule size than present in conventional infant formulae, was administered, it was observed that later in life the body composition was changed, resulting in less fat mass and less fat mass relative to total body weight and an increased lean body mass compared to the body composition upon administering conventional infant formula. In particular the visceral obesity, which is most associated with health problems, was reduced. In particular the adipocte hypertrophy was reduced. Obesity caused by adipocyte hypertrophy is thought to be indicative for onset of obesity later in life and is more associated with health problems such as insulin resistance than obesity caused by adipocyte hyperplasia.

The important difference between the investigated formulae was the size of the lipid globules, whereas the fatty acid profile was similar in the formulae.

The investigated formulae further enabled a similar good growth and development early in life and more particularly had no effect on fat mass early in life. So there was no direct effect, e.g. an obesity preventive effect, of the diet. This is advantageous since in infants and young children fat mass has important roles in energy storage, insulation, storage of fat soluble vitamins and hormonal development, such as the development of leptin and insulin sensitivity and it is therefore not desired to decrease fat mass in infants and young children.

An even improved effect on fat mass, and fat mass relative to total body mass later in life was observed when the large lipid globules were coated by an outer layer of polar lipids. This improvement could not be explained by the presence of the polar lipids itself, since mere addition of polar lipids without coating of the lipid globules did not show these improved effects.

Standard infant milk formulae have vegetable fat as lipid component. The lipid is homogenized in order to create a stable emulsion and the lipid globules are small, with a volume-weighted mode diameter of about 0.3-0.6 μm. Less than 55 volume % based on total lipid, typically less than 35 vol. %, has a size between 2 and 12 μm. The lipid globules are for a large part covered with milk proteins, in particular casein.

The present invention relates to infant formulae or growing up milks for toddlers comprising vegetable fats with a lipid globule size larger than that of standard infant formulae. The present composition comprises lipid globules with a lipid volume-weighted mode diameter of above 1.0 μm, preferably between 1.0 and 10 μm, and/or with at least 45, more preferably at least 55 volume % with a diameter of 2 to 12 μm based on total lipid. This can be achieved upon homogenizing of the lipid component comprising vegetable fat at lower pressures, preferably in the presence of polar lipids in order to coat the enlarged lipid globules and make them more stable. It was found that the thus obtained oil in water emulsion is stable for at least 48 h. Especially when the formulae is dried to a powder and subsequently reconstituted with water to a ready to drink formula shortly before use, no disadvantageous effects regarding stability are observed.

It has now surprisingly been found that the size of the lipid globule administered early in life is one of the determining factors which affect body composition, in particular fat mass, more particular visceral fat mass, and lean body mass, later in life. This effect on fat mass was even more pronounced when the large lipid globules were coated with polar lipids such as phospholipids. Since advantageously no acute effects of the diet on body composition were observed, it is concluded that the diet programmed or imprinted the body in such a way that it resulted in the development of an improved body composition later in life after further growth under similar conditions.

The present invention therefore can be used for food compositions intended for infants and/or toddlers in order to prevent obesity, visceral obesity, increase lean body mass and/or decrease fat mass later in life.

DETAILED DESCRIPTION

The present invention thus concerns a method for prevention of obesity, reducing the risk of obesity, and/or treatment of obesity, said method comprising administering to a human subject a nutritional composition comprising
- a) 10 to 50 wt. % vegetable lipids based on dry weight of the composition, and
- b) lipid globules
  - i) with a volume-weighted mode diameter above 1.0 μm, preferably between 1.0 and 10 μm, and/or
  - ii) with a diameter of 2 to 12 μm in an amount of at least 45, more preferably at least 55 volume % based on total lipid.

For sake of clarity it is noted that the lipid globules as defined under b) comprise vegetable lipids as defined under a) or in other words that a) and b) overlap.

Also the present invention concerns a method for improving body composition, the improvement of body composition being selected from the group consisting of increased lean body mass, decreased fat mass, and decreased relative fat mass, said method comprising administering to a human subject a nutritional composition comprising
- a) 10 to 50 wt. % vegetable lipids based on dry weight of the composition, and
- b) lipid globules
  - i) with a volume-weighted mode diameter above 1.0 μm, preferably between 1.0 and 10 μm, and/or
  - ii) with a diameter of 2 to 12 μm in an amount of at least 45, more preferably at least 55 volume % based on total lipid.

In one aspect the present invention relates to a non-therapeutic method for prevention of obesity and/or reducing the risk of obesity, said method comprising administering to a human subject a nutritional composition comprising
- a) 10 to 50 wt. % vegetable lipids based on dry weight of the composition, and
- b) lipid globules
  - i) with a volume-weighted mode diameter above 1.0 μm, preferably between 1.0 and 10 μm, and/or
  - ii) with a diameter of 2 to 12 μm in an amount of at least 45, more preferably at least 55 volume % based on total lipid.

Also in a further aspect the present invention relates to a non-therapeutic method for improving body composition, the improvement of body composition being selected from the group consisting of increased lean body mass, decreased fat mass, and decreased relative fat mass, said method comprising administering to a human subject a nutritional composition comprising
- a) 10 to 50 wt. % vegetable lipids based on dry weight of the composition, and
- b) lipid globules
  - i) with a volume-weighted mode diameter above 1.0 μm, preferably between 1.0 and 10 μm, and/or
  - ii) with a diameter of 2 to 12 μm in an amount of at least 45, more preferably at least 55 volume % based on total lipid.

The present invention can also be worded as the use of lipid for the manufacture of a nutritional composition for prevention of obesity, reducing the risk of obesity, and/or treatment of obesity, said nutritional composition comprising
- a) 10 to 50 wt. % vegetable lipids based on dry weight of the composition, and
- b) lipid globules
  - i) with a volume-weighted mode diameter above 1.0 μm, preferably between 1.0 and 10 μm, and/or
  - ii) with a diameter of 2 to 12 μm in an amount of at least 45, more preferably at least 55 volume % based on total lipid.

The invention also concerns the use of lipid for the manufacture of a nutritional composition for improving body composition, the improvement of body composition being selected from the group consisting of increased lean body mass, decreased fat mass, and decreased relative fat mass, said nutritional composition comprising
- a) 10 to 50 wt. % vegetable lipids based on dry weight of the composition, and
- b) lipid globules
  - i) with a volume-weighted mode diameter above 1.0 μm, preferably between 1.0 and 10 μm, and/or
  - ii) with a diameter of 2 to 12 μm in an amount of at least 45, more preferably at least 55 volume % based on total lipid.

The present invention can also be worded as a nutritional composition comprising
- a) 10 to 50 wt. % vegetable lipids based on dry weight of the composition, and
- b) lipid globules
  - i) with a volume-weighted mode diameter above 1.0 μm, preferably between 1.0 and 10 μm, and/or
  - ii) with a diameter of 2 to 12 μm in an amount of at least 45, more preferably at least 55 volume % based on total lipid.

for use in prevention of obesity, reducing the risk of obesity, and/or treatment of obesity.

The invention also concerns a nutritional composition comprising
- a) 10 to 50 wt. % vegetable lipids based on dry weight of the composition, and
- b) lipid globules
  - i) with a volume-weighted mode diameter above 1.0 μm, preferably between 1.0 and 10 μm, and/or
  - ii) with a diameter of 2 to 12 μm in an amount of at least 45, more preferably at least 55 volume % based on total lipid for use in improving body composition, the improvement of body composition being selected from the group consisting of increased lean body mass, decreased fat mass, and decreased relative fat mass.

Further the invention relates to a nutritional composition comprising
- a) 10 to 50 wt. % vegetable lipids based on dry weight of the composition, and
- b) lipid globules
  - i) with a volume-weighted mode diameter above 1.0 μm, preferably between 1.0 and 10 μm, and/or
  - ii) with a diameter of 2 to 12 μm in an amount of at least 45 volume %, more preferably at least 55 volume % based on total lipid, and
- c) 0.5-20 wt. % phospholipids based on total lipid, wherein the phospholipids are derived from milk lipids.

Further the invention relates to a nutritional composition comprising
- a) 10 to 50 wt. % vegetable lipids based on dry weight of the composition, and b) lipid globules
   i) with a volume-weighted mode diameter above 1.0 μm, preferably between 1.0 and 10 μm, and/or
   ii) with a diameter of 2 to 12 μm in an amount of at least 45 volume %, more preferably at least 55 volume % based on total lipid, and
c) 0.6 to 25 wt. % of polar lipids based on total lipids, wherein polar lipids are the sum of phospholipids, glycosphingolipids and cholesterol based on total lipid.

Also the invention relates to a process for making a nutritional composition comprising the steps of
a) providing an aqueous mixture comprising lipids, wherein the lipids comprise 50 to 100 wt. % vegetable lipid based on total lipid and wherein 0.2 to 20 wt. % based on total lipid is phospholipid, and comprising protein, digestible carbohydrate, and optionally non-digestible oligosaccharide, and
b) homogenizing said mixture in two steps with 5-100 bar, preferably 30-100 bar in the first step and 5-50 bar in the second step, and
c) preferably sterilizing said homogenized mixture and
d) preferably spray drying said sterilized mixture.

A sterilization step can also be performed prior to step b). In this case step c) preferably is omitted. Thus in one embodiment the process according to the invention comprises a step a1) of sterilizing the aqueous mixture obtained in step a).

Obesity

The present composition is preferably administered to a human subject with an age below 36 months, preferably below 18 months, more preferably below 12 months, even more preferably below 6 months. Preferably the human subject is not obese and/or not suffering from overweight.

Obesity in the present invention relates to an excess of body fat mass. Fat mass is also known as adipose tissue or fat tissue. An adult human person suffers from obesity if over 25 wt. % (for man) or over 30 wt. % (for women) of body weight is fat mass. Obesity is sometimes referred to as adiposity.

Suitable ways to determine % body fat mass are underwater weighing, skin fold measurement, bioelectrical impedance analysis, computed tomography (CT/CAT scan), magnetic resonance imaging (MRI/NMR), ultrasonography and dual energy X-ray absorptiometry (DEXA). A preferred method is DEXA measurement. In the context of this invention body fat mass is determined by DEXA.

The increased risk of health problems later in life, such as diabetes and cardiovascular diseases, is related to the occurrence of visceral adiposity and not to general obesity. The term 'visceral obesity' refers to a condition with increased visceral fat tissue. Visceral adiposity is typically caused by (accumulation of) excessive visceral fat tissue. Visceral fat, also known as organ fat, intra-abdominal fat, peritoneal fat or central fat, is normally located inside the peritoneal cavity as opposed to subcutaneous fat which is found underneath the skin and intramuscular fat which is found interspersed in skeletal muscles. Visceral fat includes the abdominal fat surrounding the vital organs and includes mesenteric fat, perirenal fat, retroperitoneal fat and preperitoneal fat (fat surrounding the liver). A waist circumference above 102 cm in adult man or above 88 cm in adult women indicates the presence of visceral adiposity. Hip-waist ratio's exceeding 0.9 in man and 0.85 in women indicate visceral adiposity. For children of 3-19 years old appropriate cutoffs for age- and sex-dependent waist circumferences can be found in Taylor et al, 2000 Am J Clin Nutr 72:490-495. A subject suffers from visceral adiposity when it meets one or more of the above criteria (regarding VAT, waist circumference or waist-hip ratio thresholds).

Lipid Component

The present composition comprises lipid. The lipid provides preferably 30 to 60% of the total calories of the composition. More preferably the present composition comprises lipid providing 35 to 55% of the total calories, even more preferably the present composition comprises lipid providing 40 to 50% of the total calories. When in liquid form, e.g. as a ready-to-feed liquid, the composition preferably comprises 2.1 to 6.5 g lipid per 100 ml, more preferably 3.0 to 4.0 g per 100 ml. Based on dry weight the present composition preferably comprises 10 to 50 wt. %, more preferably 12.5 to 40 wt. % lipid, even more preferably 19 to 30 wt. % lipid.

Lipids include polar lipids (such as phospholipids, glycolipids, sphingomyelin, and cholesterol), monoglycerides, diglycerides, triglycerides and free fatty acids. Preferably the composition comprises at least 75 wt. %, more preferably at least 85 wt. % triglycerides based on total lipids.

The lipid of the present invention comprises vegetable lipids. The presence of vegetable lipids advantageously enables an optimal fatty acid profile, high in (poly)unsaturated fatty acids and/or more reminiscent to human milk fat. Using lipids from cow's milk alone, or other domestic mammals, does not provide an optimal fatty acid profile. This less optimal fatty acid profile, such as a large amount of saturated fatty acids, is known to result in increased obesity. Preferably the present composition comprises at least one, preferably at least two lipid sources selected from the group consisting of linseed oil (flaxseed oil), rape seed oil (such as colza oil, low erucic acid rape seed oil and canola oil), salvia oil, perilla oil, purslane oil, lingonberry oil, sea buckthorn oil, hemp oil, sunflower oil, high oleic sunflower oil, safflower oil, high oleic safflower oil, olive oil, black currant seed oil, echium oil, coconut oil, palm oil and palm kernel oil. Preferably the present composition comprises at least one, preferably at least two lipid sources selected from the group consisting of linseed oil, canola oil, coconut oil, sunflower oil and high oleic sunflower oil. Commercially available vegetable lipids are typically offered in the form a continuous oil phase. When in liquid form, e.g. as a ready-to-feed liquid, the composition preferably comprises 2.1 to 6.5 g vegetable lipid per 100 ml, more preferably 3.0 to 4.0 g per 100 ml. Based on dry weight the present composition preferably comprises 10 to 50 wt. %, more preferably 12.5 to 40 wt. % vegetable lipid, even more preferably 19 to 30 wt. %. Preferably the composition comprises 50 to 100 wt. % vegetable lipids based on total lipids, more preferably 70 to 100 wt. %, even more preferably 75 to 97 wt. %. It is noted therefore that the present composition also may comprise non-vegetable lipids. Suitable and preferred non-vegetable lipids are further specified below.

Lipid Globule Size

According to the present invention, lipid is present in the composition in the form of lipid globules, emulsified in the aqueous phase. The lipid globules of the present invention have
1. a volume-weighted mode diameter above 1.0 μm, preferably above 3.0 μm, more preferably 4.0 μm or above, preferably between 1.0 and 10 μm, more preferably between 2.0 and 8.0 μm, even more preferably between 3.0 and 8.0 μm, most preferably between 4.0 and 8.0 μm and/or
2. a size distribution in such a way that at least 45 volume %, preferably at least 55 volume %, even more preferably at least 65 volume %, even more preferably at least 75 volume % has a diameter between 2 and 12 μm. More preferably at least 45 volume %, preferably at least 55 volume %, even more preferably at least 65 volume %, even more preferably at least 75 volume % has a diameter between 2 and 10 µm. Even more preferably at least 45 volume %, preferably at least 55 volume %, even more preferably at least 65 volume %, even more preferably at least 75 volume % has a diameter between 4 and 10 µm.

The percentage of lipid globules is based on volume of total lipid. The mode diameter relates to the diameter which is the most present based on volume of total lipid, or the peak value in a graphic representation, having on the X-as the diameter and on the Y-as the volume (%). The volume of the lipid globule and its size distribution can suitably be determined using a particle size analyzer such as a Mastersizer (Malvern Instruments, Malvern, UK), for example by the method described in Michalski et al, 2001, Lait 81: 787-796.

Polar Lipids

The present invention preferably comprises polar lipids. Polar lipids are amphipathic of nature and include glycerophospholipids, glycosphingolipids, sphingomyelin and/or cholesterol. More preferably the composition comprises phospholipids (the sum of glycerophospholipids and sphingomyelin). Polar lipids in the present invention relate to the sum of glycerophospholipids, glycosphingolipids, sphingomyelin and cholesterol. Preferably the polar lipids are present as a coating or outer layer of the lipid globule. The presence of polar lipids as a coating or outer layer of the lipid globule was found to advantageously further decrease fat mass and relative fat mass, i.e. obesity. The presence of polar lipids helps to maintain the lipid globules emulsified in the aqueous composition. This is especially important when the lipid globule size is large. Thus in one embodiment according to the present invention the lipid globules are coated with a layer of phospholipids or polar lipids. Thus preferably the lipid globules comprise a core and a coating. The core comprises vegetable fat and preferably comprises at least 90 wt. % triglycerides and more preferably essentially consists of triglycerides. The coating comprises phospholipids and/or polar lipids. Not all phospholipids and/or polar lipids that are present in the composition need necessarily be comprised in the coating, but preferably a major part is. Preferably more than 50 wt. %, more preferably more than 70 wt. %, even more preferably more than 85 wt. %, most preferably more than 95 wt. % of the phospholipids and/or polar lipids that are present in the composition are comprised in the coating of lipid globules. Not all vegetable lipids that are present in the composition need necessarily be comprised in the core of lipid globules, but preferably a major part is, preferably more than 50% wt. %, more preferably more than 70 wt. %, even more preferably more than 85 wt. %, even more preferably more than 95 wt. %, most preferably more than 98 wt. % of the vegetable lipids that are present in the composition are comprised in the core of lipid globules.

The present composition preferably comprises glycerophospholipids. Glycerophospholipids are a class of lipids formed from fatty acids esterified at the hydroxyl groups on carbon-1 and carbon-2 of the backbone glycerol moiety and a negatively-charged phosphate group attached to carbon-3 of the glycerol via an ester bond, and optionally a choline group (in case of phosphatidylcholine, PC), a serine group (in case of phosphatidylserine, PS), an ethanolamine group (in case of phosphatidylethanolamine, PE), an inositol group (in case of phosphatidylinositol, PI) or a glycerol group (in case of phosphatidylglycerol, PG) attached to the phosphate group. Lysophospholipids are a class of phospholipids with one fatty acyl chain. Preferably the present composition contains PC, PS, PI and/or PE, more preferably at least PC. Preferably the glycerophospholipids comprise negatively charged phospholipids in particular PS and/or PI. Negatively charged glycerophospholipids advantageously improve the stability of the oil in water emulsion.

The present composition preferably comprises glycosphingolipids. The term glycosphingolipids as in the present invention particularly refers to glycolipids with an amino alcohol sphingosine. The sphingosine backbone is O-linked to a charged headgroup such as ethanolamine, serine or choline backbone. The backbone is also amide linked to a fatty acyl group. Glycosphingolipids are ceramides with one or more sugar residues joined in a β-glycosidic linkage at the 1-hydroxyl position. Preferably the present composition contains gangliosides, more preferably at least one ganglioside selected from the group consisting of GM3 and GD3.

The present composition preferably comprises sphingomyelin. Sphingomyelins have a phosphorylcholine or phosphorylethanolamine molecule esterified to the 1-hydroxy group of a ceramide. They are classified as phospholipid as well as sphingolipid, but are not classified as a glycerophospholipid nor as a glycosphingolipid.

Sphingolipids are in the present invention defined as the sum of sphingomyelin and glycosphingolipids. Phospholipids are in the present invention defined as the sum of sphingomyelin and glycerophospholipids. Preferably the phospholipids are derived from milk lipids. Preferably the weight ratio of phospholipids:glycosphingolipids is from 2:1 to 10:1, more preferably 2:1 to 5:1.

Preferably the present composition comprises phospholipids. Preferably the present composition comprises 0.2 to 20 wt. % phospholipids based on total lipid, more preferably 0.5 to 20 wt. % phospholipids based on total lipid, more preferably 0.5 to 10 wt. %, more preferably 1 to 10 wt. %, even more preferably 3 to 8 wt. %. Preferably the present composition comprises 0.1 to 10 wt. % glycosphingolipids based on total lipid, more preferably 0.5 to 5 wt. %, even more preferably 2 to 4 wt %. Preferably the present composition comprises 0.3 to 20 wt. % (glycosphingolipids plus phospholipids) based on total lipid, more preferably 0.5 to 20 wt. % (glycosphingolipids plus phospholipids) based on total lipid, more preferably 1 to 10 wt. %.

The present composition preferably comprises cholesterol. The present composition preferably comprises at least 0.005 wt. % cholesterol based on total lipid, more preferably at least 0.02 wt. %, more preferably at least 0.05 wt. %., even more preferably at least 0.1 wt. %. Preferably the amount of cholesterol does not exceed 10 wt. % based on total lipid, more preferably does not exceed 5 wt. %, even more preferably does not exceed 1 wt. % of total lipid.

Preferably the present composition comprises 0.3 to 25 wt. % polar lipids based on total lipid, wherein the polar lipids are the sum of phospholipids, glycosphingolipids, and cholesterol, more preferably 0.6 to 25 wt. % polar lipids based on total lipid, more preferably 0.6 to 12 wt. %, more preferably 1 to 10 wt. %, even more preferably 3 to 10 wt. %.

Preferred sources for providing the phospholipids, glycosphingolipids and/or cholesterol are egg lipids, milk fat, buttermilk fat and butter serum fat (such as beta serum fat). A preferred source for phospholipids, particularly PC, is soy lecithin and/or sunflower lecithin. The present composition preferably comprises phospholipids derived from milk. Preferably the present composition comprises phospholipids and glycosphingolipids derived from milk. Preferably also cholesterol is obtained from milk. Preferably the polar lipids are derived from milk. Polar lipids derived from milk include the polar lipids isolated from milk lipid, cream lipid, butter serum lipid (beta serum lipid), whey lipid, cheese lipid and/or buttermilk lipid. The buttermilk lipid is typically obtained during the manufacture of buttermilk. The butter serum lipid or beta serum lipid is typically obtained during the manufacture of anhydrous milk fat from butter. Preferably the phospholipids, glycosphingolipids and/or cholesterol are obtained from milk cream. The composition preferably comprises phospholipids, glycosphingolipids and/or cholesterol from milk of cows, mares, sheep, goats, buffalos, horses and camels. It is most preferred to use a lipid extract isolated from cow's milk. Polar lipids derived from fat milk advantageously decrease fat mass to a larger extent than polar lipids from other sources. Preferably the polar lipids are located on the surface of the lipid globule, i.e. as a coating or outer layer. A suitable way to determine whether the polar lipids are located on the surface of the lipid globules is laser scanning microscopy as described in example 1. The concomitant use of polar lipids derived from domestic animals milk and trigycerides derived from vegetable lipids therefore enables to manufacture lipid globules with an architecture more similar to human milk, while at the same time providing an optimal fatty acid profile. Suitable commercially available sources for milk polar lipids are BAEF, SM2, SM3 and SM4 powder of Corman, Salibra of Glanbia, and LacProdan MFGM-10 or PL20 from Arla. Preferably the source of milk polar lipids comprises at least 4 wt. % phospholipids based on total lipid, more preferably 7 to 75 wt. %, most preferably 20 to 70 wt. % phospholipids based on total lipid.

Preferably the weight ratio phospholipids to protein is above 0.10, more preferably above 0.20, even more preferably above 0.3. Preferably at least 25 wt. %, more preferably at least 40 wt. %, most preferably at least 75 wt. % of the polar lipids is derived from milk polar lipids.

Fatty Acid Composition

Herein LA refers to linoleic acid and/or acyl chain (18:2 n6); ALA refers to α-linolenic acid and/or acyl chain (18:3 n3); LC-PUFA refers to long chain polyunsaturated fatty acids and/or acyl chains comprising at least 20 carbon atoms in the fatty acyl chain and with 2 or more unsaturated bonds; DHA refers to docosahexaenoic acid and/or acyl chain (22:6, n3); EPA refers to eicosapentaenoic acid and/or acyl chain (20:5 n3); ARA refers to arachidonic acid and/or acyl chain (20:4 n6); DPA refers to docosapentaenoic acid and/or acyl chain (22:5 n3). Medium chain fatty acids (MCFA) refer to fatty acids and/or acyl chains with a chain length of 6, 8 or 10 carbon atoms.

LA preferably is present in a sufficient amount in order to promote a healthy growth and development, yet in an amount as low as possible to prevent occurrence of obesity later in life. The composition therefore preferably comprises less than 15 wt. % LA based on total fatty acids, preferably between 5 and 14.5 wt. %, more preferably between 6 and 10 wt. %. Preferably the composition comprises over 5 wt. % LA based on fatty acids. Preferably ALA is present in a sufficient amount to promote a healthy growth and development of the infant. The present composition therefore preferably comprises at least 1.0 wt. % ALA based on total fatty acids.

Preferably the composition comprises at least 1.5 wt. % ALA based on total fatty acids, more preferably at least 2.0 wt. %. Preferably the composition comprises less than 10 wt. % ALA, more preferably less than 5.0 wt. % based on total fatty acids. The weight ratio LA/ALA should be well balanced in order to prevent obesity, while at the same time ensuring a normal growth and development. Therefore, the present composition preferably comprises a weight ratio of LA/ALA between 2 and 15, more preferably between 2 and 7, more preferably between 4 and 7, more preferably between 3 and 6, even more preferably between 4 and 5.5, even more preferably between 4 and 5.

Since MCFA contribute to a reduced fat mass later in life when administered to an infant, the present composition preferably comprises at least 3 wt. % MCFA based on total fatty acids, more preferably at least 10 wt. %, even more preferably 15 wt. %. Since MCFA reduces body fat deposition with no preference for central fat mass, and since MFCA does not decrease the number of adipocytes, the present composition advantageously comprises less than 50 wt. % MCFA based on total fatty acids, more preferably less than 40 wt. %, even more preferably less than 25 wt. %.

Preferably the present composition comprises n-3 LC-PUFA, since n-3 LC-PUFA reduce obesity later in life, more preferably central obesity. More preferably, the present composition comprises EPA, DPA and/or DHA, even more preferably DHA. Since a low concentration of DHA, DPA and/or EPA is already effective and normal growth and development are important, the content of n-3 LC-PUFA in the present composition, preferably does not exceed 15 wt. % of the total fatty acid content, preferably does not exceed 10 wt. %, even more preferably does not exceed 5 wt. %. Preferably the present composition comprises at least 0.2 wt. %, preferably at least 0.5 wt. %, more preferably at least 0.75 wt. %, n-3 LC-PUFA of the total fatty acid content.

As the group of n-6 fatty acids, especially arachidonic acid (AA) and LA as its precursor, counteracts the group of n-3 fatty acids, especially DHA and EPA and ALA as their precursor, the present composition comprises relatively low amounts of AA. The n-6 LC-PUFA content preferably does not exceed 5 wt. %, more preferably does not exceed 2.0 wt. %, more preferably does not exceed 0.75 wt. %, even more preferably does not exceed 0.5 wt. %, based on total fatty acids. Since AA is important in infants for optimal functional membranes, especially membranes of neurological tissues, the amount of n-6 LC-PUFA is preferably at least 0.02 wt. % more preferably at least 0.05 wt. %, more preferably at least 0.1 wt. % based on total fatty acids, more preferably at least 0.2 wt. %. The presence of AA is advantageous in a composition low in LA since it remedies LA deficiency. The presence of, preferably low amounts, of AA is beneficial in nutrition to be administered to infants below the age of 6 months, since for these infants the infant formulae is generally the only source of nutrition.

Preferably in addition to the vegetable lipid, a lipid selected from fish oil (preferably tuna fish oil) and single cell oil (such as algal, microbial oil and fungal oil) is present. These sources of oil are suitable as LC-PUFA sources. Preferably as a source of n-3 LC-PUFA single cell oil, including algal oil and microbial oil, is used, since these oil sources have a low EPA/DHA ratio, which results in an increased anti-obesity effect. More preferably fish oil (even more preferably tuna fish oil) is used as a source of n-3 LC-PUFA since they have a higher EPA concentration which is advantageous since EPA is precursor of eicosanoids which have an additional anti-obesity effect. Thus in one embodiment the present composition further comprises at least one lipid selected from the group consisting of fish oil, marine oil, algal oil, fungal oil and microbial oil.

Process for Obtaining Lipid Globules

The present composition comprises lipid globules. The lipid globule size can be manipulated by adjusting process steps by which the present composition is manufactured. A suitable and preferred way to obtain larger lipid globule sizes is to adapt the process of homogenization. In standard infant milk formula the lipid fraction (usually comprising vegetable fat, a small amount of polar lipids and fat soluble vitamins) is mixed into the aqueous fraction (usually comprising water, skimmed milk, whey, digestible carbohydrates such as lactose, water soluble vitamins and minerals and optionally non-digestible carbohydrates) by homogenization. If no homogenization was to take place, the lipid part would cream very quickly, i.e. separate from the aqueous part and collect at the top. Homogenization is the process of breaking up the fat phase into smaller sizes so that it no longer quickly separates from the aqueous phase but is maintained in a stable emulsion. This is accomplished by forcing the milk at high pressure through small orifices.

However, the present inventors found that homogenization at a lower pressure than usually applied in the preparation of infant formula resulted in the larger lipid globules of the present invention, while maintaining a sufficiently stable emulsion.

The process comprises the following steps:

1 Mixing Ingredients

The ingredients of the composition are mixed, e.g. preferably blended. Basically a lipid phase, comprising the vegetable lipids, and an aqueous phase are added together. The ingredients of the aqueous phase may comprise water, skimmed milk (powder), whey (powder), low fat milk, lactose, water soluble vitamins and minerals. Preferably the aqueous phase comprises protein, digestible carbohydrates, and polar lipids, more preferably phospholipids. Preferably the aqueous phase comprises non-digestible oligosaccharides. Preferably the aqueous phase is set at a pH between 6.0 and 8.0, more preferably pH 6.5 to 7.5. Preferably the polar lipids, in particular the phospholipids are derived from milk. The presence of polar lipids advantageously results in more stable lipid globules. This is especially important in case of larger lipid globules. Advantageously, having polar lipids present in the aqueous mixture before homogenization results in coating of the lipid globules, consisting essentially of triglycerides, with a layer of polar lipids.

Preferably the lipid phase comprises 50 to 100 wt. % vegetable lipids based on total weight of the lipid phase. Instead of in the aqueous phase, the polar lipids, more preferably the phospholipids, may also be present in the lipid phase or in both phases. Alternatively the polar lipids may be added separately to an aqueous and lipid phase. Preferably, the weight ratio of phospholipid to total lipid is from 0.2 to 20 wt. %, more preferably from 0.5 to 10 wt. %, even more preferably 3 to 8 wt. % 0.2.

The aqueous and lipid phase are preferably heated before adding together, preferably at a temperature of 40° C. to 80° C., more preferably 55° C. to 70° C., even more preferably 55° C. to 60° C. The mixture is also kept at this temperature and blended. A suitable way for blending is using an Ultra-Turrax T50 for about 30-60 s at 5000-10000 rpm. Subsequently demi-water may be added to this blend, to obtain the desired dry matter %. A desired dry matter % is for example 15%. Alternatively, the lipid phase is injected to the aqueous phase immediately prior to homogenization. It is preferred that injection is performed immediate before homogenization and under a low pressure in order to obtain stable large lipid globules.

Minerals, vitamins, and stabilizing gums may be added at various points in the process depending on their sensitivity to heat. Mixing can for instance be performed with a high shear agitator. In the process of the present invention, skimmed milk (casein) is preferably not present in this step and added to the composition after homogenization of the fat fraction into the aqueous fraction (comprising compounds such as whey, whey protein, lactose).

2 Pasteurization

Preferably the mixture is then pasteurized. Pasteurization involves a quick heating step under controlled conditions which microorganisms cannot survive. A temperature of 60 to 80° C., more preferably 65 to 75° C., held for at least 15 s, usually adequately reduces vegetative cells of microorganisms. Several pasteurization methods are known and commercially feasible. Alternatively this step can also be performed before mixing as in step 1 and/or be replaced by the heating step to 60° C. in step 1.

3 Homogenization

Subsequently the optionally pasteurized mixture is homogenized. Homogenization is a process which increases emulsion uniformity and stability by reducing the size of the lipid globules in the formula. This process step can be performed with a variety of mixing equipment, which applies high shear to the product. This type of mixing breaks the lipid globules into smaller globules. The mixture obtained is preferably homogenized in two steps at high temperature and pressure, for example 60° C. at 30 to 100 and 5 to 50 bar respectively, with a total pressure of 35 to 150 bar. Alternatively, the mixture obtained is preferably homogenized in two steps at a lower temperature, between 15 and 40° C., preferably about 20° C. at 5 to 50 and 5 to 50 bar respectively, with a total pressure of 5 to 100 bar. In one embodiment, the mixture obtained is homogenized at 30-100 bar in the first step. In another embodiment, the mixture obtained is homogenized at 5-50 bar in the first step.

This is remarkably lower than standard pressures, which typically are 250 to 50 bar, respectively, so a total pressure of 300 bar.

It will be dependent on the specific homogenizer used, which pressure to apply. A suitable way is to use a pressure of 100 bar in the first step and 50 bar in the second step in a Niro Suavi NS 2006 H Homogenizer at a temperature of 60° C. A suitable way is to use a pressure of 5 bar in the first step and 20 bar in the second step in a Niro Suavi NS 2006 H Homogenizer at a temperature of 20° C. Subsequently optionally other ingredients, not being lipid, may be added.

4 Sterilization

Subsequently, the emulsion obtained in step 3 is preferably sterilized. Preferably sterilization takes place in-line at ultra high temperature (UHT) and/or in appropriate containers to obtain a formula in the form of a sterile liquid. A suitable way for UHT treatment is a treatment at 120-130° C. for at least 20 s. Alternatively, the emulsion obtained in step 3 is concentrated by evaporation, subsequently sterilized at ultra high temperature and subsequently spray dried to give a spray dried powder which is filled into appropriate containers.

Alternatively this sterilization step is performed before the homogenization step. Preferably the composition obtained by the above process is spray dried afterwards.

The difference on coating of the lipid globules can further be derived from the zeta potential. Zeta potential ($\zeta$ potential) measures the difference in milliVolts (mV) in electrokinetic potential between the tightly bound layer around the surface and the distant zone of electroneutrality and is a measure of the magnitude of the repulsion or attraction between particles in a dispersion. Its value is also related to the stability of colloidal dispersions. A high absolute zeta potential will confer stability, i.e. the solution or dispersion will resist aggregation.

Digestible Carbohydrate Component

The composition preferably comprises digestible carbohydrate. The digestible carbohydrate preferably provides 30 to 80% of the total calories of the composition. Preferably the digestible carbohydrate provides 40 to 60% of the total calories. When in liquid form, e.g. as a ready-to-feed liquid, the composition preferably comprises 3.0 to 30 g digestible carbohydrate per 100 ml, more preferably 6.0 to 20, even more preferably 7.0 to 10.0 g per 100 ml. Based on dry weight the present composition preferably comprises 20 to 80 wt. %, more preferably 40 to 65 wt. % digestible carbohydrates.

Preferred digestible carbohydrate sources are lactose, glucose, sucrose, fructose, galactose, maltose, starch and maltodextrin. Lactose is the main digestible carbohydrate present in human milk. The present composition preferably comprises lactose. The present composition preferably comprises digestible carbohydrate, wherein at least 35 wt. %, more preferably at least 50 wt. %, more preferably at least 75 wt. %, even more preferably at least 90 wt. %, most preferably at least 95 wt. % of the digestible carbohydrate is lactose. Based on dry weight the present composition preferably comprises at least 25 wt. % lactose, preferably at least 40 wt. %.

Non-Digestible Oligosaccharides

Preferably the present composition comprises non-digestible oligosaccharides with a degree of polymerization (DP) between 2 and 250, more preferably 3 and 60. The non-digestible oligosaccharides advantageously prevent the onset of insulin resistance, which also will result in a reduced obesity and/or fat mass later in life. Furthermore, the presence of non-digestible oligosaccharides advantageously results in an intestinal microbiota low in Firmicutes and high in Bacteroidetes, which results in a reduced obesity. Therefore the non-digestible oligosaccharides are presumed to enhance the anti-obesity effects of the larger lipid globules of the composition according to the present invention.

The non-digestible oligosaccharide is preferably selected from the group consisting of fructo-oligosaccharides (such as inulin), galacto-oligosaccharides (such as transgalacto-oligosaccharides or beta-galacto-oligisaccharides), gluco-oligosaccharides (such as gentio-, nigero- and cyclodextrin-oligosaccharides), arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid comprising oligosaccharides and uronic acid oligosaccharides. Preferably the composition comprises gum acacia on combination with a non-digestible oligosaccharide.

Preferably the present composition comprises fructo-oligosaccharides, galacto-oligosaccharides and/or galacturonic acid oligosaccharides, more preferably galacto-oligosaccharides, most preferably transgalacto-oligosaccharides. In a preferred embodiment the composition comprises a mixture of transgalacto-oligosaccharides and fructo-oligosaccharides. Preferably the present composition comprises galacto-oligosaccharides with a DP of 2-10 and/or fructo-oligosaccharides with a DP of 2-60. The galacto-oligosaccharide is preferably selected from the group consisting of transgalacto-oligosaccharides, lacto-N-tetraose (LNT), lacto-N-neotetraose (neo-LNT), fucosyl-lactose, fucosylated LNT and fucosylated neo-LNT. In a particularly preferred embodiment the present method comprises the administration of transgalacto-oligosaccharides ([galactose]$_n$-glucose; wherein n is an integer between 1 and 60, i.e. 2, 3, 4, 5, 6, . . . , 59, 60; preferably n is selected from 2, 3, 4, 5, 6, 7, 8, 9, or 10). Transgalacto-oligosaccharides (TOS) are for example sold under the trademark Vivinal™ (Borculo Domo Ingredients, Netherlands). Preferably the saccharides of the transgalacto-oligosaccharides are β-linked.

Fructo-oligosaccharide is a non-digestible oligosaccharide comprising a chain of β linked fructose units with a DP or average DP of 2 to 250, more preferably 10 to 100. Fructo-oligosaccharide includes inulin, levan and/or a mixed type of polyfructan. An especially preferred fructo-oligosaccharide is inulin. Fructo-oligosaccharide suitable for use in the compositions is also already commercially available, e.g. Raftiline®HP (Orafti).

Uronic acid oligosaccharides are preferably obtained from pectin degradation. Uronic acid oligosaccharides are preferably galacturonic acid oligosaccharides. Hence the present composition preferably comprises a pectin degradation product with a DP between 2 and 100. Preferably the pectin degradation product is prepared from apple pectin, beet pectin and/or citrus pectin. Preferably the composition comprises transgalacto-oligosaccharide, fructo-oligosaccharide and a pectin degradation product. The weight ratio transgalacto-oligosaccharide:fructo-oligosaccharide:pectin degradation product is preferably (20 to 2):1:(1 to 3), more preferably (12 to 7):1:(1 to 2).

Preferably, the composition comprises of 80 mg to 2 g non-digestible oligosaccharides per 100 ml, more preferably 150 mg to 1.50 g, even more preferably 300 mg to 1 g per 100 ml. Based on dry weight, the composition preferably comprises 0.25 wt. % to 20 wt. %, more preferably 0.5 wt. % to 10 wt. %, even more preferably 1.5 wt. % to 7.5 wt. %. A lower amount of non-digestible oligosaccharides will be less effective in preventing obesity, whereas a too high amount will result in side-effects of bloating and abdominal discomfort.

Protein Component

The present composition preferably comprises proteins. The protein component preferably provides 5 to 15% of the total calories. Preferably the present composition comprises a protein component that provides 6 to 12% of the total calories. More preferably protein is present in the composition below 9% based on calories, more preferably the composition comprises between 7.2 and 8.0% protein based on total calories, even more preferably between 7.3 and 7.7% based on total calories. A low protein concentration advantageously ensures a lower insulin response, thereby preventing proliferation of adipocytes in infants. Human milk comprises a lower amount of protein based on total calories than cow's milk. The protein concentration in a nutritional composition is determined by the sum of protein, peptides and free amino acids. Based on dry weight the composition preferably comprises less than 12 wt. % protein, more preferably between 9.6 to 12 wt. %, even more preferably 10 to 11 wt. %. Based on a ready-to-drink liquid product the composition preferably comprises less than 1.5 g protein per 100 ml, more preferably between 1.2 and 1.5 g, even more preferably between 1.25 and 1.35 g.

The source of the protein should be selected in such a way that the minimum requirements for essential amino acid content are met and satisfactory growth is ensured. Hence protein sources based on cows' milk proteins such as whey, casein and mixtures thereof and proteins based on soy, potato or pea are preferred. In case whey proteins are used, the protein source is preferably based on acid whey or sweet whey, whey protein isolate or mixtures thereof and may include α-lactalbumin and β-lactoglobulin. More preferably, the protein source is based on acid whey or sweet whey from which caseino-glyco-macropeptide (CGMP) has been removed. Removal of CGMP from sweet whey protein advantageously reduces the threonine content of the sweet whey protein. A reduced threonine content is also advantageously achieved by using acid whey. Optionally the protein source may be supplemented with free amino acids, such as methionine, histidine, tyrosine, arginine and/or tryptophan in order to improve the amino acid profile. Preferably α-lactalbumin enriched whey protein is used in order to optimize the amino acid profile. Using protein sources with an optimized amino acid profile closer to that of human breast milk enables all essential amino acids to be provided at reduced protein concentration, below 9% based on calories, preferably between 7.2 and 8.0% based on calories and still ensure a satisfactory growth. If sweet whey from which CGMP has been removed is used as the protein source, it is preferably supplemented by free arginine in an amount of from 0.1 to 3 wt. % and/or free histidine in an amount of from 0.1 to 1.5 wt. % based on total protein.

Preferably the composition comprises at least 3 wt. % casein based on dry weight. Preferably the casein is intact and/or non-hydrolyzed.

Nutritional Composition

The present composition is preferably particularly suitable for providing the daily nutritional requirements to a human with an age below 36 months, particularly an infant with the age below 24 months, even more preferably an infant with the age below 18 months, most preferably below 12 months of age. Hence, the nutritional composition is for feeding or is used for feeding a human subject. The present composition comprises a lipid, and preferably a protein and preferably a digestible carbohydrate component wherein the lipid component preferably provides 30 to 60% of total calories, the protein component preferably provides 5 to 20%, more preferably 5 to 15 wt. %, of the total calories and the digestible carbohydrate component preferably provides 25 to 75% of the total calories. Preferably the present composition comprises a lipid component providing 35 to 50% of the total calories, a protein component provides 6 to 12% of the total calories and a digestible carbohydrate component provides 40 to 60% of the total calories. The amount of total calories is determined by the sum of calories derived from protein, lipids and digestible carbohydrates.

The present composition is not human breast milk. The present composition comprises vegetable lipids. The compositions of the invention preferably comprise other fractions, such as vitamins, minerals according to international directives for infant formulae.

In one embodiment the composition is a powder suitable for making a liquid composition after reconstitution with an aqueous solution, preferably with water. Preferably the composition is a powder to be reconstituted with water. It was surprisingly found that the size and the coating with polar lipids of the lipid globules remained the same after the drying step and subsequent reconstitution. The presence of larger lipid globules may have a slightly negative effect on the long term stability of the liquid composition. However, separation of the lipid and aqueous layers was not observed within 48 h, which is much longer than the time between reconstituting the powder to a ready to drink liquid and the consumption of it, which will be less than 24 h and typically within 1 h. The composition being in a powder form has therefore an additional advantage in the present invention with large lipid globules.

In order to meet the caloric requirements of the infant, the composition preferably comprises 50 to 200 kcal/100 ml liquid, more preferably 60 to 90 kcal/100 ml liquid, even more preferably 60 to 75 kcal/100 ml liquid. This caloric density ensures an optimal ratio between water and calorie consumption. The osmolarity of the present composition is preferably between 150 and 420 mOsmol/l, more preferably 260 to 320 mOsmol/l. The low osmolarity aims to reduce the gastrointestinal stress. Stress can induce adipocyte formation.

Preferably the composition is in a liquid form, with a viscosity below 35 mPa·s, more preferably below 6 mPa·s as measured in a Brookfield viscometer at 20° C. at a shear rate of 100 $s^{-1}$. Suitably, the composition is in a powdered from, which can be reconstituted with water to form a liquid, or in a liquid concentrate form, which should be diluted with water. When the composition is in a liquid form, the preferred volume administered on a daily basis is in the range of about 80 to 2500 ml, more preferably about 450 to 1000 ml per day.

Infant

Adipocytes proliferate during the first 36 months of life as well as more limited in puberty. The amount of adipocytes is an important determinant in the degree of fat mass, adipose tissue and/or obesity later-in-life. Hence the present composition is preferably administered to the human subject during the first 3 years of life. In one embodiment of the use according to the present invention, the nutritional composition is for feeding a human subject with an age between 0 and 36 months. It was found that there is a predominance of proliferation of adipocytes in the first 12 months of life with an optimum in perinatal adipocyte proliferation. Hence, it is particularly preferred that the present composition is administered to a human subject in this period of life. The present composition is therefore advantageously administered to a human of 0-24 months, more preferably to a human of 0-18 months, most preferably to a human of 0-12 months. The present invention particularly aims to prevent obesity later-in-life and is preferably not an obesity treatment. Hence, the present composition is preferably administered to an infant and/or toddler not suffering from obesity or overweight. In one embodiment of the use according to the present invention, the nutritional composition is for feeding a non-obese human subject. Preferably the composition is to be used in infants having a weight appropriate for gestational age. Although the adipocyte proliferation is most pronounced during the first 36 months of life and puberty, adipocytes are formed also to al lesser degree in the interval between 36 months and puberty. So in one embodiment the present composition is preferably administered to an age up to 5 years, more preferably up to 10 years, more preferably up to 13 years.

Preferably the composition is to be used in infants which are prematurely born or which are small for gestational age. These infants experience after birth a catch up growth, which is an extra risk for developing obesity and/or too much fat mass later in life. Preferably the composition is to be used in infants which are large for gestational age. These infants have an increased risk of developing obesity and/or too much fat mass later in life. Preferably the composition is to be used in infants born from mothers who suffer from obesity and/or diabetes. Such infants have an increased risk of developing obesity and/or too much fat mass later in life.

Application

The present composition is preferably administered orally to the infant. The present invention also aims to prevent the occurrence of obesity and/or reduce the fat mass at the age above 36 months. In one embodiment the present method is for preventing obesity, reducing the risk of obesity and/or for improving body composition of a human subject when said human subject has an age above 36 months, preferably when said human subject has an age above 5 years, particularly above 13 years, more particularly above 18 years. In one embodiment the present method or the present nutritional composition is for feeding a human subject with an age between 0 and 36 months and for preventing obesity, reducing the risk of obesity and/or for improving body composition when said human subject has an age above 36 months, preferably to prevent obesity, reduce the risk of obesity and/or improve body composition at the age above 5 years, particularly above 13 years, more particularly above 18 years. In one embodiment the prevention of obesity, reduction of the risk of obesity and/or improving of body composition occurs later in life. With later in life is meant an age exceeding the age at which the diet is taken, preferably exceeding said age with at least one year. In one embodiment the present method or the present nutritional composition is for preventing visceral obesity and/or for reducing the ratio visceral fat to subcutaneous fat.

The inventors surprisingly found that when mice during infancy and childhood were fed a food composition comprising enlarged lipid globules, a different and significant effect on body composition later in life was observed compared to mice which during infancy and childhood had been fed a food composition having a similar fatty acid composition, but a smaller lipid globule size. At day 42, which is a time point corresponding to childhood in a human setting, no difference was observed in growth (weight) between the two groups, but from day 42 both groups were fed a Western style diet which was high in fat. Surprisingly at day 126, which is a time point corresponding to adulthood in humans, the mice, which had previously consumed the food composition of the present invention before turning to the Western style diet, had a significantly lower fat mass and lower relative fat mass than mice which had received a control composition. It was in further experiments demonstrated that the presence of a coating or outer layer of polar lipids around these dietary lipid globules even further decreased fat mass and relative fat mass compared to large lipid globules without this coating. It was also surprisingly found that compared to the control diet, administering a diet comprising large lipid globules during infancy resulted in a specific decrease of visceral fat mass later in life, i.e. resulted in reduced visceral obesity later in life. This is advantageous, since in particular visceral obesity is most associated with health problems. Furthermore, it was observed that the adipocte hypertrophy was reduced. Obesity caused by adipocyte hypertrophy is thought to be indicative for onset of obesity later in life and is more associated with health problems such as insulin resistance than obesity caused by adipocyte hyperplasia. This is a further indication that the diet does not have an acute effect on treatment or prevention of obesity (which is unwanted in infants) but a programming effect to prevent the occurrence of obesity later in life.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

EXAMPLES

Example 1

Process for Preparing an IMF with Larger Lipid Globule Size

Example 1A

An infant formula was prepared comprising per kg powder 4800 kcal, 248 g lipid, 540 g digestible carbohydrates, 55 g non-digestible oligosaccharides and 103 g protein. The composition was prepared using BAEF powder (Corman, Goé, Belgium), a vegetable oil blend, demineralised whey powder, lactose, non-digestible oligosaccharides (galacto-oligosaccharides and long chain fructo-oligosaccharides in a weight ratio of 9/1). Also vitamins, minerals, trace elements as known in the art were used.

The amount of BAEF was such that 7.24 wt. % phospholipids (from BAEF) based on total lipids were present in the composition. Based on a small amounts of phospholipids in the oil blend, the total amount of phospholipids was 7.39 wt. % based on total lipid. BAEF also supplied a small amount of cholesterol (about 0.08 wt. % based on total lipid of the infant formula) and glycosphingolipids (about 1.65% glycosphingolipids based on total lipid of the infant formula). The BAEF powder was mixed with galacto-oligosaccharides, lactose, vitamin pre-mixtures and mineral premixes in water, at room temperature, by stiffing. Potassium hydroxide was used to set the pH at 6.8-7.0. The dry weight matter of the mixture was about 27%. The mixture was heated to 60° C. The vegetable oil blend was also heated to 60° C. and added to the water phase and blended with an Ultra-Turrax T50 for about 30-60 s at 5000-10000 rpm. Subsequently demi-water was added to achieve a dry matter content of about 15%.

Subsequently the oil-water mixture was homogenised at a pressure of 100 bar in a first step and 50 bar in a second step in a Niro Suavi NS 2006 H Homogenizer. The temperature was 60° C. Subsequently demineralized whey powder was added to arrive at a final dry matter content of 18%. The product was UHT treated at 125° C. for 30 s. The product was dried to a powder by spray drying. Maltodextrin together with long chain inulin was blended dry into the powder. The size of the lipid globules was measured with a Mastersizer 20000 (Malvern Instruments, Malvern UK). The volumetric mode diameter was 7.3 µm. A second, much smaller peak was present at 0.52 µm. The volume % of lipid globules with a size between 2 and 12 m was 71% based on total lipid volume. It was checked with confocal laser scanning microscopy that the larger lipid globules of the present invention were coated with phospholipids, before spray drying and after reconstitution of the spray dried powder with water. In both cases the lipid globules were covered with a layer of phospholipids. As fluorescent probes Annexin V Alexa Fluor 488 (In Vitrogen molecular probes) for labeling the phospholipids, and Nile Red (Sigma-Aldrich) for labeling triglycerides, were used. After labeling the milk samples Vectrahield mounting medium (Vector laboratories inc., Burliname USA) for reducing particle movement and photo-bleaching was added. Observations were made using a Zeiss Laser Scanning Microscope with excitation wavelengths of 488/543/633 nm and emission filters set at band pass 505-530, and band pass 560-615. Also the size of the lipid globules was the same before drying and after reconstitution of the spray dried powder with water.

As a control the lipid globules of a standard infant formula (Nutrilon 1) did not show labeling with phospholipids as observed with the confocal laser scanning microscopy. Instead the globules were covered with protein, as determined with the fluorescent protein stain Fast Green FCF. The volumetric modal diameter of the lipid globules in this standard infant milk formula was measured to be 0.5 µm. A second much smaller peak was present at 8.1 µm. The volume % of lipid globules with a size between 2 and 12 m was 34% based on total lipid volume.

TABLE 1

Lipid globule characteristics of different milks

|  | Volume Mode diameter μm | Volume % with a diameter between 2 and 12 μm | ζ potential (mV) |
|---|---|---|---|
| Standard infant milk formula (Nutrilon 1) | 0.5 | 34 | −22.4 |
| Infant milk formula of the invention | 7.3 | 71 | −16 |
| Human milk | 5.3 | 98 | −13.8 |

Also human milk was analyzed and showed a volumetric modal diameter of the lipid globules of 5.3 μm. The volume % of lipid globules with a size between 2 and 12 m was 98% based on total lipid volume. The lipid globules were covered with a layer of phospholipids.

The zeta potentials and volume weighted mean diameters were also measured. The results are shown in table 1.

Example 1B

Infant formula were prepared similar to example 1A. The oil blend was prepared using vegetable oils, oil soluble vitamins and antioxidants. Both the water phase and the oil blend were heated to 65° C. prior to mixing. The oil blend was added to the water phase and blended with an Ultra-Turrax T50 for about 30-60 s at 5000-1000 rpm. The dry weight of this mixture was about 26%. The product was UHT treated for 30 s at 125° C. and subsequently cooled to 20° C.

For diet 2 and 3 and 4 this mixture was homogenized in two steps at a pressure of 5 and 20 bar respectively in a Niro Suavi NS 2006 H homogenizer. For diet 1 the homogenization pressure was 200 and 50 bar, respectively in a Niro Suavi NS 2006 H homogenizer. The products were dried to a powder by spray drying. Long chain inulin was blended dry into the powder. For diet 1 and 2 no added polar lipids were present. The amount of vegetable glycerophospholipids was 0.2 wt. % based on total fat for diet 1 and 2. Diet 1 and 2 did not contain sphingolipids and cholesterol. For diet 3 and 4 a butter milk powder was used. Diet 3 comprised 1.83 wt. % glycerophospholipids based on total fat, of which about 90% derived from the butter milk powder and about 10% already present in the standard IMF derived from vegetable oils, and further comprised milk derived sphingolipids of which the majority (about 0.47 wt. % based on total fat) was sphingomyelin; the rest being glycosphingolipids, of which the majority (over 60%) is GD3 with a concentration of about 0.13 wt. % based on total fat. Diet 3 comprised about 0.05 wt. % milk derived cholesterol based on total fat. Diet 4 comprised half of the amount of milk derived polar lipids based on total fat of diet 3.

In diet 3 the butter milks powder comprising these polar lipids were dry blended after the homogenization, sterilization and spray dry step in order to prevent coating of the lipid globules.

In diet 4 the butter polar lipids were present in the aqueous phase during the homogenization step in order to coat the lipid globules.

The size of the lipid globules was measured with a Mastersizer 20000 (Malvern Instruments, Malvern UK) and shown in Table 2. Coating of the lipid globules with polar lipids in diet 4 and absence of coating in diet 1, 2 and 3 was confirmed by the confocal laser scanning microscopy method as described above.

TABLE 2

Lipid globule characteristics of different milks

| IMF | Volume Mode diameter μm | Volume % with a diameter between 2 and 12 μm |
|---|---|---|
| 1, Standard IMF | 0.5 | 5.1 |
| 2, Experimental IMF (large lipid globules) | 4.0 | 72.2 |
| 3, Experimental IMF (large lipid globules, free polar lipids) | 5.0 | 74.8 |
| 4, Experimental IMF (large lipid globules coated with polar lipids) | 4.3 | 70.3 |

After 5 months storage at room temperature the size of the lipid globules in diet 1 had not changed, with a volume mode diameter of 0.5. Also the volume mode diameter of diet 2, 3 and 4 were rather stable being 4.8 μm, 7.9 μm and 6.6 μm respectively.

Example 2

Programming Effect of Lipid Globule Size on Adult Body Composition

Offspring of C57/BL6 dams were weaned from day 15 on. The experimental weaning diets were continued until day 42. From day 42 to day 126 all pups were fed the same diet based on AIN-93G diet with an adjusted lipid fraction (containing 10 wt. % lipid of which 50 wt. % lard and 1% cholesterol, based on total lipid), which is representative for a Western style diet.

The experimental diets that were used for weaning were:
1) an infant milk formula (IMF) based control diet. This diet comprised 282 g standard IMF (Nutrilon 1) per kg, with the lipid globule size as mentioned in example 1A. The rest of the diet was AIN-93G protein, carbohydrates and fibre. All lipid present in the diet was derived from the IMF.
2) an IMF based diet of the present invention. This diet differed from diet 1 in that it comprised 282 g IMF of example 1A, i.e. comprised lipid globules larger than the control. All lipid present in the diet was derived from the IMF.

At day 42, all mice switched to a "Western style diet" comprising 10 wt. % lipid until day 126. The composition of the diets is given in table 3. The fatty acid composition of the two experimental and cafeteria diet is shown in table 4. The fatty acid profile of the two experimental diets was very similar.

TABLE 3 composition of experimental diets per kg

|  | Diet 1, Control IMF | Diet 2, IMF of the invention | Western style diet |
|---|---|---|---|
| Kcal | 3922 | 3922 | 4016 |
| Lipid (g) | 70 | 70 | 100 |
| Phospholipids (g) | 0.12 | 5.16 | n.d. |
| Cholesterol (g) | 0.00 | 0.06 | 1 |
| Digestible Carbohydrates (g) | 644 | 644 | 600 |
| Lactose (g) | 145.9 | 145.9 | 0 |
| Sucrose, glucose (g) | 85 | 85 | 150 |
| Maltodextrin (g) | 360 | 360 | 450 |
| Fiber (g) | 47.5 | 47.5 | 47.5 |
| Protein | 179 | 179 | 179 | n.d. = not determined

The mice were weighed twice a week. The food intake was determined once a week during the entire experiment. To determine body composition (i.e., fat mass (FM) and fat-free mass (FFM)) DEXA scans (Dual Energy X-ray Absorbiometry) were performed under general anesthesia at 6, 10 and 14 weeks of age, 42, 70, 98 and 126 days after birth respectively, by densitometry using a PIXImus imager (GE Lunar, Madison, Wis., USA). At the age of 126 days the male mice were sacrificed and organs were dissected and weighed (i.e. fat tissues, liver, Muscle tibialis). Blood was analyzed for leptin, resistin, and (fasting) insulin.

TABLE 4

Fatty acid composition of the experimental diets

| | Diet 1, Control IMF | Diet 2, IMF of the invention | Western style diet |
|---|---|---|---|
| C12:0 | 9.4 | 8.7 | 5.3 |
| C14:0 | 4.4 | 5.3 | 2.7 |
| C16:0 | 18.7 | 21.3 | 23.1 |
| C18:0 | 3.5 | 5.2 | 9.0 |
| C18:1 n-9 | 39.9 | 37.7 | 40.5 |
| C18:2 n-6 (LA) | 15.7 | 12.6 | 11.9 |
| C18:3 n-3 (ALA) | 2.4 | 2.1 | 1.3 |
| Others | 6.0 | 7.1 | 6.7 |
| n-6 | 16.0 | 12.9 | 11.9 |
| n-3 | 2.4 | 2.1 | 1.3 |
| n-6/n-3 | 6.58 | 6.12 | 9.1 |
| LA/ALA | 6.46 | 6.00 | 9.15 |
| SFA | 39.3 | 44.4 | 41.9 |
| MFA | 42.1 | 39.8 | 42.3 |
| PUFA | 18.3 | 14.9 | 13.2 |

Results:

No effect on growth (body weight) and food intake was observed during the experimental period between the groups. Moreover, the development of fat mass (determined with DEXA) was not significantly different at day 42 (end of the diet intervention period).

A subsequent treatment with a Western style diet between day 42 and day 126 of all groups resulted in clear differences in body composition at the end of the experiment (day 126), see Table 5. The fat mass and relative fat mass developed later in life was reduced in the pups which had received the diet with the larger lipid globules during their infancy and childhood, compared to pups which had received the control diet. The overall body weight was comparable between the two groups. The experimental group had an increased lean body mass.

TABLE 5

Body weight, lean body mass, fat mass and relative fat mass.

| Parameter | Day | Diet 1, Control IMF | Diet 2, IMF of the invention |
|---|---|---|---|
| Bodyweight g | 42 | 23.50 (0.45) | 24.24 (0.51) |
| Mean (s.e.) | 70 | 29.88 (0.46) | 30.16 (0.77) |
| | 98 | 33.32 (0.57) | 33.69 (0.95) |
| | 126 | 34.47 (0.80) | 34.15 (1.16) |
| Lean body mass g | 42 | 18.96 (0.34) | 19.96 (0.40)* |
| Mean (s.e.) | 70 | 21.31 (0.42) | 22.32 (0.48) |
| | 98 | 22.22 (0.49) | 23.91 (0.45)* |
| | 126 | 23.30 (0.43) | 24.19 (0.53)* |
| Fat mass g | 42 | 3.78 (0.13) | 3.77 (0.21) |
| Mean (s.e.) | 70 | 7.84 (0.35) | 7.13 (0.65) |
| | 98 | 10.68 (0.53) | 9.19 (0.79)* |
| | 126 | 10.48 (0.67) | 9.11 (0.90)* |
| Fat % of body weight | 42 | 16.59 (0.45) | 15.83 (0.68) |
| Mean (s.e.) | 70 | 26.89 (1.07) | 23.81 (1.61) |
| | 98 | 32.38 (1.42) | 27.25 (1.67)* |
| | 126 | 30.78 (1.42) | 26.67 (1.77)* |

*$P < 0.05$ compared to control group

The liver in the control group had a mean weight of 157 g (s.e. 0.07) and in the experimental diet 1.44 g (s.e. 0.15). This is indicative for a reduced fatty liver in the experimental group. The Muscle tibialis was 95.3 g (mean, with s.e. 2.1) in the control group and 96.7 g (s.e. 3.2) in the experimental group. This corresponds with the effects on lean body mass. The effects on fat tissues is shown in Table 6. In the experimental group the animals showed a higher amount of brown adipose tissue (BAT), but lower amounts of white adipose tissues (WAT), such as the retroperitoneal (rp), inguinal (i) and epididymal (e) fat. The presence of brown adipose tissue is advantageous for infants for insulation purposes. White adipose tissue is present in adults as well as infants and is used for energy storage. Lower visceral fat mass (i.e. eWAT and rpWAT) is also advantageous, since it will decrease the risk of insulin insensitivity or insulin resistance.

TABLE 6

Adipose tissue mass in mice on day 126.

| Fat tissue | Diet 1, Control IMF | Diet 2, IMF of the invention |
|---|---|---|
| BAT mg mean (s.e.) | 150.0 (9.0) | 180.4 (16.5) |
| rpWAT mg mean (s.e.) | 379.0 (31.6) | 349.3 (35.5) |
| iWAT mg mean (s.e.) | 772.3 (43.9) | 665.5 (50.5) |
| eWAT mg mean (s.e.) | 1380 (100) | 1300 (130) |

Fasting insulin levels were lower in the experimental group (1200 units) than in the control group (1470 units). This is indicative for a reduced adipocyte signal. Leptin levels were decreased in the experimental group (6000 units) compared to the control group (9500). Resistin was also decreased in the experimental group (1350) compared to the control group (1550). This is indicative for a normal appetite and a reduced tendency for adiposity, i.e. increased fat mass, respectively.

These results demonstrate that the fat mass, relative fat mass and/or obesity in later life clearly is decreased by an early in life diet with increased lipid globule size. It is concluded that food comprising lipid globules with an altered lipid architecture program and/or imprint the body early in life in such a way that later in life a healthier body composition develops, with less fat mass, relative fat mass and/or with increased lean body mass.

Example 3

Programming Effect of Lipid Globule Size on Adult Body Composition

The same experimental animal model and set up was used as in example 2, except that the experiment was terminated at day 98 instead of day 128.

The experimental diets that were used for weaning were:
1) an infant milk formula (IMF) based control diet. This diet comprised 282 g standard IMF per kg, IMF 1 of example 1B, i.e. small lipid globules, and no added polar lipids. The rest of the diet was AIN-93G protein, carbohydrates and fibre. All lipid present in the diet was derived from the IMF.

2) an IMF based diet of the present invention. This diet differed from diet 1 in that it comprised 282 g IMF 2 of example 1B, i.e. comprised lipid globules larger than the control and no added polar lipids. All lipid present in the diet was derived from the IMF.

3) an IMF based diet of the present invention with added phospholipids. This diet differed from diet 2 in that it comprised 282 g IMF 3 of example 1B, i.e. comprised lipid globules larger than the control and added polar lipids, not located at the outer surface layer of the lipid globule. All lipid present in the diet was derived from the IMF.

4) an IMF based diet of the present invention. This diet differed from diet 3 in that it comprised 282 g IMF 4 of example 1B, i.e. comprised lipid globules larger than the control coated with polar lipids derived from milk. All lipid present in the diet was derived from the IMF.

The composition of the diets is similar as in table 3 of example 2. The fatty acid composition of the two experimental and cafeteria diet is similar as in table 4 of example 2, with calculated linoleic acid (LA) of 14% in diet 1 and 2 and 13.2% in diet 3 and 4 based on total fatty acids, with alpha linoleinc acid (ALA) of 2.6 in diet 1 and 2 and 2.5.% in diet 3 and 4 based on total fatty acids and with LA/ALA of 5.4 in diet 1 and 2 and 5.3, in diet 3 and 4 respectively. The amount of DHA was 0.2 wt. % in all 4 diets, and the amount of ARA was 0.35 wt. % in diet 1 and 2 and 0.36 wt. % in diet 3 and 4.

Results:

No effect on growth (body weight) and food intake was observed during the experimental period between the groups. Moreover, the development of body weight and fat mass (determined with DEXA) was not significantly different at day 42 (end of the diet intervention period).

A subsequent treatment with a Western style diet between day 42 and day 98 of all groups resulted in clear differences in body composition at the end of the experiment (day 98), see Table 7. The fat mass and relative fat mass developed later in life was reduced in the mice which had received the diet with the larger lipid globules during their infancy and childhood, compared to mice which had received the control diet.

TABLE 7

Fat mass and relative fat mass.

| Parameter | Day | Diet 1 | Diet 2 | Diet 3 | Diet 4 |
|---|---|---|---|---|---|
| Fat mass g | 98 | 8.35 (0.67) | 7.29 (0.37) | 7.93 (0.52) | 6.43 (0.66)* |
| Mean (s.e.) | Delta 98-42 | 3.93 (0.61) | 3.10 (0.39) | 3.96 (0.58) | 2.40 (0.68)* |
| Fat % of body | 98 | 26.31 (1.33) | 24.18 (0.83) | 25.48 (1.19) | 22.48 (1.29)* |
| weight Mean (s.e.) | Delta 98-42 | 8.88 (1.28) | 7.21 (0.83) | 9.42 (1.23) | 5.93 (1.44)* |

*P < 0.05

From the results above it can be deduced that increase in size of lipid globule results in decreased fat mass and relative fat mass (compare diet 1 versus diet 2). The decrease in fat mass and relative fat mass is even higher when the lipid globules are coated with polar lipids derived from milk lipids (compare diet 4 with diet 1 or 2). This improved effect is considered not only to be due to the polar lipids it itself, but can possibly also be attributed to the coating of the lipid globules, since with diet 3 the effects are much less pronounced as in with diet 4.

TABLE 8

Adipose tissue mass in mice on day 98.

| Fat tissue | Diet 1 | Diet 2 | Diet 3 | Diet 4 |
|---|---|---|---|---|
| iWAT* mean (s.e.) | 520 (40) | 550 (40) | 500 (30) | 410 (30) |
| periWAT mean (s.e.) | 64 (8) | 41 (5) | 57 (7) | 47 (6) |
| Rp WAT mean (s.e.) | 280 (30) | 280 (20) | 270 (20) | 230 (30) |
| eWAT mean (s.e.) | 1070 (110) | 1010 (70) | 980 (80) | 870 (110) |
| iWAT/ (periWAT + rpWAT) | 1.51 | 1.71 | 1.53 | 1.48 |

*WAT: white adipose tissue
i: inguinal
rp: retroperitoneal
peri: perirenal
e: epididymal The effect on fat tissues is shown in Table 8. Larger lipid globules resulted especially in decreased visceral fat (perirenal fat and epididymal fat) compared to subcutaneous fat (compare diet 1 with diet 2).

White adipose tissue is present in adults as well as infants and is used for energy storage. Lower visceral fat mass (i.e. eWAT and rpWAT) is advantageous, since it will decrease the risk of insulin insensitivity or insulin resistance.

In the adipose tissues (eWAT and iWAT) of mice fed with diet 1 and diet 4 the cell size was determined at day 98. Adipocytes were isolated and the mean diameter was determined by image analysis of microscopic pictures. The volume was calculated as $V=(\pi/6)(3\sigma+X^2)X$ where X and $\sigma^2$ are the mean and the variance of the diameter. The mean volume of adipocytes in eWAT, representative of visceral fat, of mice fed with diet 1 was $5.1\ 10^6\ \mu m^3$ (s.e. $0.56\ 10^6$) and of mice fed diet 4 was $4.3\ 10^6\ \mu m^3$ (s.e. $0.52\ 10^6$). The mean volume of adipocytes in iWAT, representative of subcutaneous fat, was less. In mice fed with diet 1 it was $2.0\ 10^6\ \mu m^3$ (s.e. $0.16\ 10^6$) and of mice fed diet 4 was $1.7\ 10^6\ \mu m^3$ (s.e. $0.1.4\ 10^6$). The number of cells was slightly higher in the diet 4 fed mice. No differences were observed in % lipid content and lipid density of the adipose fat mass.

These results demonstrate that the fat mass, relative fat mass and/or obesity in later life clearly is decreased by an early in life diet with increased lipid globule size. These effects are even more pronounced when the large lipid globules are coated with polar lipids. Furthermore, larger lipid globules resulted in a specific effect in reducing visceral obesity. It is concluded that food comprising lipid globules with an altered lipid architecture program and/or imprint the body early in life in such a way that later in life during growth under similar circumstances a healthier body composition develops, with less fat mass, and/or relative fat mass.

Example 4

Infant Nutrition with Larger Lipid Globules Size

An infant formula comprising per kg powder 4810 kcal, 255 g lipid, 533 g digestible carbohydrates, 58 g non-digestible oligosaccharides (galacto-oligosaccharides and long chain fructo-oligosaccharides in a weight ratio of 9/1), 96 g protein, and vitamins, minerals, trace elements as known in the art.

The lipid composition is such that 0.57 wt. % of the lipid is composed of phospholipids. The composition comprises about 0.17 wt. % glycosphingolipids based on total lipid. The composition comprises about 0.006 wt. % cholesterol based on total lipids. As a source of phospholipids, glycosphingolipids and cholesterol SM-2 powder (Corman, Goé, Belgium) is used. About 97-98% of the lipid is vegetable lipid, the rest being milk fat, fish oil and microbial oil. The amount of LC-PUFA is about 0.64 wt. % based on total fatty acids. The LA/ALA ratio is 5.2.

Homogenization was performed similar as in example 1. The volumetric mode diameter was above 1 μm. The volume % of lipid globules with a size between 2 and 12 m was above 45% based on total lipid volume.

The invention claimed is:

1. A method of preventing, reducing and or treating obesity, comprising administering to a human subject between 0 and 36 months of age and in need thereof a nutritional composition comprising:
   (i) 10 to 50 wt. % vegetable lipids based on dry weight of the composition, and polar lipids selected from a) 0.3 to 25 wt. % polar lipids based on total lipids, wherein polar lipids are the sum of phospholipids, glycosphingolipids and cholesterol, or b) 0.2 to 20 wt. % phospholipids, based on total lipids, and
   (ii) lipid globules having
      (a) a volume-weighted mode diameter above 1.0 μm, and/or
      (b) a diameter of 2 to 12 μm in an amount of at least 45 volume % based on total lipid; wherein the lipid globules are coated with phospholipids.

2. The method of claim 1, wherein the lipid globules have a volume-weighted mode diameter between 1.0 and 10 μm.

3. The method according to claim 1, wherein the lipid globules have a diameter of 2 to 12 μm in an amount of at least 55 volume % based on total lipid.

4. The method according to claim 1, wherein the subject is a human subject 36 months of age or older.

5. The method according to claim 1, wherein the subject is a human subject above 5 years of age.

6. The method according to claim 1, wherein the subject is a non-obese human subject.

7. The method according to claim 1, wherein the obesity is visceral obesity.

8. The method according to claim 1, wherein the lean body mass of the subject is increased, fat mass of the subject is decreased, and/or fat mass relative to total body weight of the subject is decreased.

9. The method according to claim 1, wherein the composition further comprises 0.6 to 25 wt. % polar lipids based on total lipid, wherein the polar lipids are the sum of phospholipids, glycosphingolipids, and cholesterol.

10. The method according to claim 1, wherein the lipid globules are coated with a layer of phospholipids and polar lipids.

11. The method according to claim 1, wherein the composition has a fatty acid profile with a linoleic acid to alpha-linolenic acid weight ratio between 4 and 7.

12. The method according to claim 1, wherein the composition further comprises at least one lipid selected from the group consisting of fish oil, marine oil, algal oil, fungal oil and microbial oil.

13. The method according to claim 1, wherein the composition further comprises 6 to 12% protein based on total calories.

14. The method according to claim 1, wherein the composition further comprises non-digestible oligosaccharides.

15. The method according to claim 1, wherein the composition is in the form of a powder.

* * * * *